United States Patent [19]

Diehr et al.

[11] Patent Number: 4,645,528
[45] Date of Patent: Feb. 24, 1987

[54] BENZOLACTAMSULTAMS

[75] Inventors: Hans-Joachim Diehr; Christa Fest, both of Wuppertal; Rolf Kirsten, Monheim; Joachim Kluth, Langenfeld; Klaus-Helmut Müller, Duesseldorf; Theodor Pfister, Monheim; Uwe Priesnitz, Solingen; Hans-Jochem Riebel, Wuppertal; Wolfgang Roy, Langenfeld; Hans-Joachim Santel, Cologne; Robert R. Schmidt, Bergisch-Gladbach, all of Fed. Rep. of Germany

[73] Assignee: Bayer Aktiengesellschaft, Leverkusen, Fed. Rep. of Germany

[21] Appl. No.: 769,280

[22] Filed: Aug. 23, 1985

[30] Foreign Application Priority Data

May 17, 1985 [DE] Fed. Rep. of Germany ....... 3517845

[51] Int. Cl.$^4$ .................... C07D 417/12; A01N 47/44
[52] U.S. Cl. .......................................... 71/90; 540/289
[58] Field of Search .......................... 260/243.3; 71/90

[56] References Cited

FOREIGN PATENT DOCUMENTS 3431920 3/1986 Fed. Rep. of Germany .......... 71/90

OTHER PUBLICATIONS

March, Advanced Org. Chem. pp. 382, 451, (1977).

Primary Examiner—Robert Gerstl
Attorney, Agent, or Firm—Sprung Horn Kramer & Woods

[57] ABSTRACT

The invention relates to novel benzolactamsultams of the general formula (I)

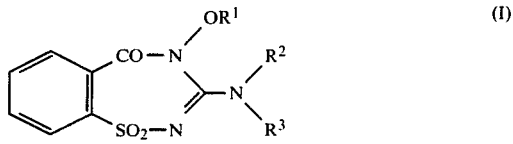

in which $R^1$ represents an optionally substituted radical from the series comprising alkyl, alkenyl, alkinyl, cycloalkyl, cycloalkylalkyl, aralkyl and aryl, $R^2$ represents hydrogen or an optionally substituted radical from the series comprising alkyl, alkenyl, alkinyl and aralkyl and $R^3$ represents the radical

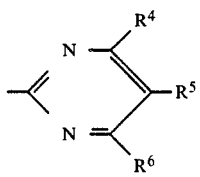

wherein $R^4$ represents hydrogen, hydroxy, halogen or an optionally substituted radical from the series comprising alkyl, alkoxy and alkylthio, $R^5$ represents hydrogen, halogen, cyano, formyl or an optionally substituted radical from the series comprising alkyl, alkylcarbonyl and alkoxycarbonyl and $R^6$ represents hydrogen, amino or an optionally substituted radical from the series comprising alkyl, alkoxy, alkylamino and dialkylamino, with the proviso that $R^4$ and $R^6$ do not simultaneously represent methyl, a process for their preparation and their use as herbicides.

10 Claims, No Drawings

BENZOLACTAMSULTAMS

The invention relates to new benzolactam-sultams, a process for their preparation and their use as herbicides.

Benzolactam-sultams have not hitherto been known from the literature. Various benzolactam-sultams are the subject of patent applications which have been filed by the Applicant Company and do not belong to the previously published prior art (compare DE-OS (German Published Specification) Nos. 3,431,915, 3,431,920 and 3,431,917).

New benzolactam-sultams of the general formula (I)

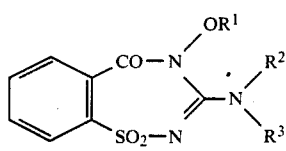

in which $R^1$ represents an optionally substituted radical from the series comprising alkyl, alkenyl, alkinyl, cycloalkyl, cycloalkylalkyl, aralkyl and aryl, $R^2$ represents hydrogen, or represents an optionally substituted radical from the series comprising alkyl, alkenyl, alkinyl and aralkyl and $R^3$ represents the radical

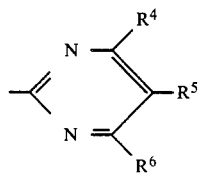

wherein $R^4$ represents hydrogen, hydroxyl or halogen or an optionally substituted radical from the series comprising alkyl, alkoxy and alkylthio, $R^5$ represents hydrogen, halogen, cyano or formyl or an optionally substituted radical from the series comprising alkyl, alkylcarbonyl and alkoxycarbonyl and $R^6$ represents hydrogen or amino or an optionally substituted radical from the series comprising alkyl, alkoxy, alkylamino and dialkylamino, with the proviso that $R^4$ and $R^6$ do not simultaneously represent methyl, have now been found.

The new compounds of the formula (I) are obtained by a process in which 2-chlorosulphonyl-benzoyl chloride of the formula (II)

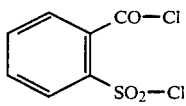

is reacted with oxyguanidine derivatives of the formula (III)

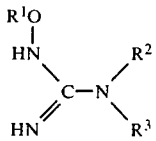

in which $R^1$, $R^2$ and $R^3$ have the abovementioned meanings, in the presence of acid acceptors and, if appropriate, in the presence of diluents.

The new benzolactam-sultams of the formula (I) are distinguished by a powerful herbicidal activity.

Surprisingly, the new compounds of the formula (I) exhibit a considerably more powerful herbicidal action than many known chemical compounds of the same type of action.

The invention preferably relates to compounds of the formula (I) in which $R^1$ represents $C_1$–$C_{12}$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl, $C_1$–$C_4$-alkoxy-carbonyl, $C_1$–$C_4$-alkylamino-carbonyl or di-($C_1$–$C_4$-alkyl)-amino-carbonyl), or represents $C_3$–$C_6$-alkenyl (which is optionally substituted by fluorine, chlorine or bromine), $C_3$–$C_6$-alkinyl, $C_3$–$C_6$-cycloalkyl, $C_3$–$C_6$-cycloalkyl-$C_1$–$C_2$-alkyl or phenyl-$C_1$–$C_2$-alkyl (which is optionally substituted by fluorine, chlorine, nitro, cyano, $C_1$–$C_4$alkyl, $C_1$–$C_4$-alkoxy or $C_1$–$C_4$-alkoxy-carbonyl) or represents phenyl (which is optionally substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxy-carbonyl), and in which, furthermore, $R^2$ represents hydrogen or $C_1$–$C_4$-alkyl (which is optionally substituted by fluorine, chlorine, cyano, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkylcarbonyl, $C_1$–$C_4$-alkoxy-carbonyl, $C_1$–$C_4$-alkylamino-carbonyl or di-($C_1$–$C_4$-alkyl)-amino-carbonyl), or represents $C_3$–$C_6$-alkenyl, $C_3$–$C_6$-alkinyl or phenyl $C_1$–$C_2$-alkyl (which is optionally substituted by fluorine, chlorine, nitro, cyano, $C_1$–$C_4$-alkyl, $C_1$–$C_4$ alkoxy or $C_1$–$C_4$-alkoxy-carbonyl), and in which, furthermore, $R^3$ represents the radical

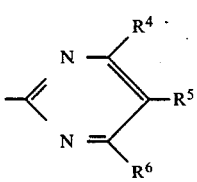

wherein $R^4$ represents hydrogen, hydroxyl, fluorine, chlorine or bromine or represents $C_1$–$C_4$-alkyl, $C_1$–$C_4$-alkoxy or $C_1$–$C_4$-alkylthio (which are optionally substituted by fluorine and/or chlorine), $R^5$ represents hydrogen, fluorine, chlorine, bromine, cyano, formyl or $C_1$–$C_4$-alkyl (which is optionally substituted by fluorine and/or chlorine) or represents $C_1$–$C_4$-alkyl-carbonyl or $C_1$–$C_4$-alkoxycarbonyl and $R^6$ represents hydrogen, amino or $C_1$-$C_4$-alkyl (which is optionally substituted by fluorine and/or chlorine) or represents $C_1$-$C_4$-alkoxy (which is optionally substituted by fluorine and/or chlorine) or represents $C_1$-$C_4$-alkyl-amino or di-($C_1$-$C_4$-alkyl)-amino, with the proviso that $R^4$ and $R^5$ do not simultaneously represent methyl.

The invention particularly relates to compounds of the formula (I) in which $R^1$ represents $C_1$-$C_8$-alkyl (which is optionally substituted by flourine or chlorine), $C_3$-$C_4$-alkenyl, $C_1$-$C_2$-alkoxy-carbonylmenthyl, phenethyl or benzyl (which is optionally substituted by fluorine, chlorine, nitro, cyano, methyl, methoxy or methoxycarbonyl), $R^2$ represents hydrogen and $R^3$ represents the radical

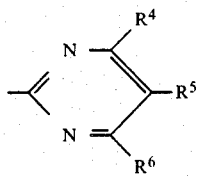

wherein $R^4$ represents hydrogen, chlorine or $C_1$-$C_2$-alkoxy (which is optionally substituted by fluorine and/or chlorine), $R^5$ represents hydrogen, methylcarbonyl or $C_1$-$C_2$-alokoxy-carbonyl and $R^6$ represents hydrogen, $C_1$-$C_2$-alkyl (which is optionally substituted by fluorine and/or chlorine) or $C_1$-$C_2$-alkoxy (which is optionally substituted by fluorine and/or chlorine).

If, for example, N'-(4-methyl-pyrimidin-2-yl)-N''-allyloxy-guanidine and 2-chlorosulphonyl-benzoyl chloride are used as starting substances in the process according to the invention, the course of the reaction can be outlined by the following equation:

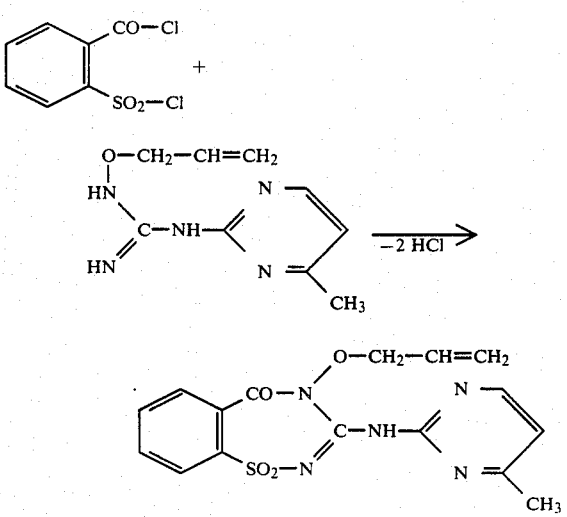

The 2-chlorosulphonyl-benzoyl chloride of the formula (II) to be used as the starting substance in the Formula (III) provides a general definition of the oxyguanidine derivatives also to be used as starting substances in the process according to the invention. In formula (III), $R^1$, $R^2$ and $R^3$ preferably or particularly have the same meanings as are given above as preferred or as particularly preferred in the context of the definition of the substituents for the formula (I).

Examples of starting substances of the formula (III) which may be mentioned are: N'-(4-methyl-pyrimidin-2-yl)-, N'-(4-methoxy-6-methyl-pyrimidin-2-yl)-, N'-(4-ethyl-pyrimidin-2-yl)-, N'-(4-ethoxy-6-methyl-pyrimidin-2-yl)-, N'-(4-chloro-6-methoxy-pyrimidin-2-yl)-, N'-(4-chloro-6-ethoxy-pyrimidin-2-yl)-, N'-(4-chloro-6-dimethylamino-pyrimidin-2-yl)-, N'-(4-methyl-6-methylthio-pyrimidin-2-yl)-, N'-(4-dimethylamino-6-methyl-pyrimidin-2-yl)-, N'-(4,6-dimethoxy-pyrimidin-2-yl)- and N'-(4-difluoromethoxy- 6-methyl-pyrimidin-2-yl)—N''-methoxy-guanidine, —N''-ethoxy-guanidine, —N''-propoxy-guanidine, —N''-isopropoxy-guanidine, —N''-butoxy-guanidine, —N''-isobutoxyguanidine, —N''-sec.-butoxy-guanidine, —N''-pentoxy-guanidine, —N''-isopentoxy-guanidine, —N''-hexyloxy-guanidine, —N''-octyloxy-guanidine, —N''-allyloxy-guanidine, —N''-(2-chloro-ethoxy)-guanidine, —N''-(2-fluoro-ethoxy)-guanidine, —N''-(2-chloro-propoxy)-guanidine, —N''-(2-fluoro-propoxy)-guanidine, —N''-(3-chloro-propoxy)-guanidine, —N''-(4-chloro-butoxy)-guanidine, —N''-methoxycarbonylmethoxy-guanidine, —N''-ethoxycarbonylmethoxy-guanidine, —N''-(1-methoxy-carbonyl-ethoxy)-guanidine, —N''-(1-ethoxycarbonylethoxy)-guanidine, —N''-(dimethylamino-carbonyl-methoxy)guanidine, —N''-(2-phenyl-ethoxy)-guanidine, —N''-phenoxyguanidine, —N''-(4-methyl-benzyloxy)-guanidine, —N''-(4-fluoro-benzyloxy)-guanidine, —N''-(4-chloro-benzyloxy)guanidine, —N''-(4-nitrobenzyloxy)-guanidine, —N''-(2,6-dichloro-benzyloxy)-guanidine, —N''-(4-methoxycarbonylbenzyloxy)-guanidine and —N''-(4-ethoxycarbonyl-benzyloxy)-guanidine.

The starting substances of the formula (III) are known in some cases (compare J. Chem. Soc. 1962, 3915 and EP-A No. 121,082).

The compounds of the formula (III) are obtained when cyanamide derivatives of the formula (IV)

in which $R^2$ and $R^3$ have the abovementioned meanings, are reacted with hydroxylamine derivatives of the formula (V)

in which $R^1$ has the abovementioned meaning, or hydrochlorides thereof, if appropriate in the presence of diluents, such as, for example, ethanol, propanol or butanol, at temperatures between 20° C. and 120° C., and, if appropriate, the reaction products are treated with acid acceptors, such as, for example, ammonia, potassium carbonate or sodium hydroxide.

The cyanamide derivatives of the formula (IV) are (a) by reaction of alkali metal or alkaline earth metal salts of cyanamide—such as, for example, sodium cyanamide or calcium cyanamide—with chloro-hetarenes of the formula (VI)

Cl-R³ (VI)

in which R³ has the abovementioned meaning, and then, if appropriate—if R² does not represent hydrogen—reaction of the product with halogen compounds of the formula (VII)

Q—R² (VII)

in which

R² represents an optionally substituted radical from the series comprising alkyl, alkenyl, alkinyl and aralkyl and Q represents chlorine, bromine or iodine, if appropriate in the presence of inert diluents, such as, for example, acetone, acetonitrile or dimethylformamide, at temperatures between 0° C. and 100° C.

After the mixture has been concentrated and the residue has been dissolved in water, the cyanamide derivatives of the formula (IV) can be precipitated by acidification, for example with hydrochloric acid, and isolated by filtration with suction.

Alternatively, the compounds of the formula (IV) are obtained (b) by reaction of cyanoguanidine ("dicyanodiamide") with β-dicarbonyl compounds or derivatives thereof, such as, for example, acetylacetone (compare J. Chem. Soc. 1953, 1725–1730), acetoacetic acid esters (compare J. Prakt. Chem. 77 (1908), 542 and J. Chem. Soc. 1948, 586) or malonic acid esters (compare German Patent Specification No. 158,591).

The 2-cyanoamino-4-hydroxy-6-methyl- and -4,6-dihydroxy-pyrimidines obtained from acetoacetic acid esters or malonic acid esters can be converted into corresponding 2-cyanoamino-4-alkoxy-6-methyl- or -4,6-dialkoxy-pyrimidines in a known manner by reaction with alkylating agents, such as, for example, dimethyl sulphate or diethyl sulphate, if appropriate in the presence of diluents, such as, for example, water, methanol, ethanol, n- and iso-propanol, acetone, dioxane or dimethylformamide, and in the presence of acid-binding agents, such as, for example, sodium hydroxide, potassium hydroxide, sodium carbonate or potassium carbonate. To avoid N-alkylation, if appropriate, acylation is carried out with an acylating agent, such as, for example, acetic anhydride or acetyl chloride, and the product is deacylated again after the alkylation with aqueous acids or bases.

In another alternative process, the compounds of the formula (IV) are obtained by a procedure in which (c) amino-hetarenes of the formula (VIII)

H₂N—R³ (VIII)

in which R³ has the abovementioned meaning, are reacted with carbonylisothiocyanates of the formula (IX)

$$R^7-\overset{\overset{O}{\|}}{C}-N=C=S \quad (IX)$$

in which R⁷ represents ethoxy or phenyl, if appropriate in the presence of an inert diluent, such as, for example, acetone, acetonitrile or toluene, at temperatures between 0° C. and 100° C., the carbonylthioureas thereby formed, of the formula (X)

$$R^7-\overset{\overset{O}{\|}}{C}-NH-\overset{\overset{S}{\|}}{C}-NH-R^3 \quad (X)$$

in which R³ and R⁷ have the abovementioned meanings, are isolated by filtration with suction, if appropriate after concentration, and are reacted with aqueous alkali metal or alkaline earth metal hydroxide solutions, such as, for example, sodium hydroxide solution, if appropriate in the presence of an organic solvent, such as, for example, tetrahydrofuran or dioxane, at temperatures between 0° C. and 120° C., and the thioureas obtained as crystals after acidification, for example with hydrochloric acid, of the formula (XI)

$$H_2N-\overset{\overset{S}{\|}}{C}-NH-R^3 \quad (XI)$$

in which R³ has the abovementioned meaning, are isolated by filtration with suction and reacted with metal compounds which can form hydrogen sulphide, such as, for example, with lead(II) acetate, copper(II) acetate, mercury(II) acetate or iron(II) acetate, in the presence of aqueous alkali metal or alkaline earth metal hydroxide solutions, such as, for example, sodium hydroxide solution, at temperatures between 20° C. and 100° C. and, after the reaction, the mixture is filtered and the filtrate is acidified with an acid, such as, for example, acetic acid. The products of the formula (IV) thereby obtained as crystals can be isolated by filtration with suction.

The starting substances for the preparation processes described above under (a), (b) and (c) for the cyanamide derivatives of the formula (IV) are known and/or can be prepared by processes which are known per se.

These include the chloro-hetarenes of the formula (VI) (compare J. Chem. Soc. (C) 1966, 2031; Chem. Pharm. Bull. 11 (1963), 1382-1388 and Arch. Pharm. 295 (1962), 649–657), the halogen compounds of the formula (VII) (commercially available chemicals), the amino-hetarenes of the formula (VIII) (compare Chem. Pharm. Bull. 11 (1963), 1382-1388; J. Chem. Soc. 1946, 81 and U.S. Pat. No. 4,299,960) and the carbonylisothiocyanates of the formula (IX) (compare J. Heterocycl. Chem. 5(1968), 837 and U.S. Pat. No. 4,160,037).

The process according to the invention for the preparation of the new compounds of the formula (1) is preferably carried out using diluents. Possible diluents are virtually all the inert organic polar solvents, but preferably aprotic polar solvents. These include optionally halogenated hydrocarbons, such as, for example, methylene chloride, chloroform, toluene and chlorobenzene, nitriles, such as, for example, acetonitrile and propionitrile, dimethylformamide, dimethylacetamide, dimethylsulphoxide, sulpholane, hexamethylphosphoric acid triamide, 1,2-dimethoxyethane, pyridine and 2-methyl-5-ethylpyridine.

Acid acceptors which can be used in the process according to the invention are virtually all the acid-binding agents which can usually be employed. These include, in particular, alkali metal and alkaline earth metal hydrides, organometallic compounds, such as butyllithium, and furthermore aliphatic, aromatic or heterocyclic amines, such as trimethylamine, triethylamine, N,N-dimethylaniline, N,N-dimethyl-benzylamine, diazabicyclooctane (DABCO), diazabicycloundecene (DBU), pyridine, 2-methyl-5-ethyl-pyridine and 4-dimethylamino-pyridine.

The reaction temperatures can be varied within a substantial range in the process according to the invention. In general, the reaction is carried out between −80° C. and +100° C., preferably between −40° C. and +50° C. The process according to the invention is in general carried out at normal pressure.

For carrying out the process according to the invention, in general between 1.0 and 1.5 moles, preferably between 1.0 and 1.2 moles, of 2-chlorosulphonyl-benzoyl chloride of the formula (II) are employed per mole of oxyguanidine derivative of the formula (III). The reaction components are usually brought together at room temperature or with external cooling and the reaction mixture is stirred until the reaction has ended.

Working up and isolation of the new compounds of the formula (I) can be carried out by customary methods. For example, the reaction mixture—if appropriate after dilution with a solvent which is virtually water-immiscible, such as, for example, ethylene chloride—is washed with dilute hydrochloric acid and with water, dried and filtered and the filtrate is concentrated. The product of the formula (I) which remains in the residue is made to crystallise by trituration with a suitable organic solvent, such as, for example, ethanol, and isolated by filtration with suction.

The active compounds according to the invention influence plant growth and can therefore be used as defoliants, desiccants, agents for destroying broad-leaved plants, germination inhibitors and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monocharia, Fimbristylis, Sagittaria, Eleocharis, Scirpus, Paspalum, Ischaemum, Spenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

The active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure and/or solid carriers, optionally with the use of surface-active agents, that is emulsifying agents and/or dispersing agents and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example petroleum fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example, ground natural minerals, such as kaolins, clays, talc, chalk, quartz, attapulgite, montmorillonite or diatomaceous earth, and ground synthetic minerals, such as highly disperse silicic acid, alumina and silicates; as solid carriers for granules there are suitable: for example, crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example, nonionic and anionic emulsifiers, such as polyoxyethylene-fatty acid esters, polyoxyethylene-fatty alcohol esters, for example alkylaryl polyglycol ethers, alkylsulphonates, alkylsulphates, arylsulphonates as well as albumin hydrolysation products; as dispersing agents there are suitable: for example, lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanin dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, N-(2-benzothiazolyl)-N,N'-dimethylurea, 3-(3-chloro-4-methylphenyl)-1,1-dimethylurea, 3-(4-isopropylphenyl)-1,1-dimethylurea, 4-amino-6-(1,1-dimethylethyl)-3-methylthio-1,2,4-triazin-5(4H)-one, 4-amino-6-(1,1-dimethyl-ethyl)-3-ethylthio-1,2,4-triazin-5(4H)-one, 1-amino-6-ethylthio-3-(2,2dimethylpropyl)- 1,3,5-triazine-2,4-(1H,3H)-dione, 4-amino-3-methyl-6-phenyl-1,2,4-triazin-5(4H)-one, 2-chloro-4-ethylamino-6-isopropylamino-1,3,5-triazine, the R-enantiomer of (trimethylsilyl)-methyl 2-[4-(3,5-dichloropyridly-2-oxy)-phenoxy]-propionate, the R-enantiomer of (2-benzyloxy)-ethyl 2-[4-(3,5-dichloropyridyl-2-oxy)phenoxy]-propionate, 2,4-dichlorophenoxyacetic acid, 2-(2,4-dichlorophenoxy)-propionic acid, 4-chloro-2-methylphenoxyacetic acid, 2-(2-methyl-4-chloro-phenoxy)propionic acid, 3,5-diiodo-4-hydroxy-benzonitrile, 3,5-dibromo-4-hydroxy-benzonitrile and diphenyl ethers and phenylpyridazines, such as, for example, pyridate. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomising or scattering.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.001 and 15 kg of active compound per hectare of soil surface, preferably between 0.005 and 10 kg per ha.

The preparation and use of the active compounds according to the invention can be seen from the following examples.

PREPARATION EXAMPLES

EXAMPLE 1

18 g (0.075 mole) of 2-chlorosulphonyl-benzoyl chloride are added dropwise to a solution of 16.1 g (0.075 mole) of N'-(4-methoxy-6-methyl-pyrimidin-2-yl)—N''-methoxy-guanidine and 13 g (0.165 mole) of pyridine in 75 ml of methylene chloride at −40° C., with stirring. The mixture is then subsequently stirred at 20° to 25° C. for 2 hours. After the methylene chloride solution has been washed with dilute hydrochloric acid and ice-water, dried and filtered and the filtrate has been concentrated, a residue is obtained, which is made to crystallise by trituration with methanol. The product thereby obtained is isolated by filtration with suction.

4.5 g (16% of theory) of the compound with the abovementioned structural formula of melting point 166° C. are obtained.

The compounds of the formula (I) listed in the following Table I can be prepared by the process described by way of example in the preceding example.

TABLE 1

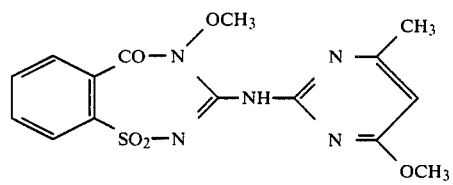

| Example No. | R$^1$ | R$^2$ | R$^3$ | Melting point [°C.] |
|---|---|---|---|---|
| 2 | —CH$_3$ | H | (pyrimidine with OCH$_3$, OCH$_3$) | 180 |
| 3 | —C$_4$H$_9$—sec. | H | (pyrimidine with OCH$_3$, OCH$_3$) | |
| 4 | —CH$_3$ | H | (pyrimidine with CH$_3$, OCHF$_2$) | |
| 5 | —CH$_3$ | H | (pyrimidine with CH$_3$, CH$_3$) | 172–173 |
| 6 | —CH$_2$—C$_6$H$_5$ | H | (pyrimidine with CH$_3$, CH$_3$) | |

TABLE 1-continued $$\text{(I)}$$
structure: benzene ring with CO—N(OR$^1$)— group and SO$_2$—N— group, connected to C(=N—)N(R$^2$)(R$^3$)

| Example No. | R$^1$ | R$^2$ | R$^3$ | Melting point [°C.] |
|---|---|---|---|---|
| 7 | —CH$_3$ | H | 4-ethyl-pyrimidin-2-yl | |
| 8 | —CH$_3$ | H | pyrimidin-2-yl | 110 |
| 9 | —C$_2$H$_5$ | H | 4-methyl-6-methoxy-pyrimidin-2-yl | |
| 10 | —C$_2$H$_5$ | H | 4,6-dimethoxy-pyrimidin-2-yl | |
| 11 | —CH$_2$—C$_6$H$_5$ | H | 4,6-dimethoxy-pyrimidin-2-yl | |
| 12 | —CH$_2$COOC$_2$H$_5$ | H | 4,6-dimethoxy-pyrimidin-2-yl | |
| 13 | —CH$_3$ | H | 4-methyl-6-ethoxy-pyrimidin-2-yl | |
| 14 | —CH$_3$ | H | 4,6-diethoxy-pyrimidin-2-yl | |
| 15 | —CH$_3$ | H | 4-methyl-6-(2,2,2-trifluoroethoxy)-pyrimidin-2-yl | |
| 16 | —CH$_2$—CH=CH$_2$ | H | 4-methyl-6-methoxy-pyrimidin-2-yl | |

Preparation of starting compounds of the formula (III)

EXAMPLE (III-1)

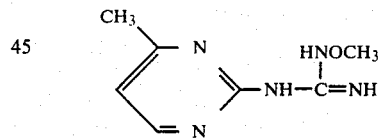

A mixture of 13.4 g (0.1 mole) of 2-cyanoamino-4-methyl-pyrimidine, 9.2 g (0.11 mole) of 0-methylhydroxylamine hydrochloride and 50 ml of ethanol is heated under reflux for 6 hours. The mixture is then filtered with suction. The filtrate is concentrated and 200 ml of water are added to the residue. The aqueous solution is brought to pH 8-pH 9 with sodium hydroxide solution. The product thereby obtained as crystals is isolated by filtration with suction.

13.1 g (72% of theory) of N'-(4-methyl-pyrimidin-2yl)—N''-methoxy-guanidine of melting point 152° C. are obtained.

The compounds of the formula (III) listed in the following Table 2 can be prepared analogously:

TABLE 2

$$\begin{array}{c} R^1O \\ | \\ HN \\ \diagdown \\ C-N \diagup\!\!\diagup R^2 \\ \diagup \quad \diagdown R^3 \\ HN \end{array} \qquad (III)$$

| Example No. | R¹ | R² | R³ | Melting point [°C.] |
|---|---|---|---|---|
| (III-2) | —C₂H₅ | H | 4-ethylpyrimidin-2-yl | |
| (III-3) | —CH₃ | H | 4-ethylpyrimidin-2-yl | 98 |
| (III-4) | —CH₂—C₆H₅ | H | 4-methylpyrimidin-2-yl | 150 |
| (III-5) | —CH₂—(2-chlorophenyl) | H | 4-methylpyrimidin-2-yl | 140 |
| (III-6) | —CH₃ | H | 4-methoxy-6-methylpyrimidin-2-yl | 126 |
| (III-7) | —CH₃ | —CH₃ | 4-methoxy-6-methylpyrimidin-2-yl | 135 |
| (III-8) | —CH₃ | H | 4-methyl-6-difluoromethoxypyrimidin-2-yl | |
| (III-9) | —CH₃ | H | 4-methyl-6-ethoxypyrimidin-2-yl | |

TABLE 2-continued $$\begin{array}{c} R^1O \\ | \\ HN \\ \diagdown \\ \phantom{xx}C-N \\ \phantom{xxx}\diagup \phantom{xx}\diagdown \\ HN \phantom{xxxxx} R^3 \end{array} \phantom{xx} \begin{array}{c} R^2 \end{array}$$ (III)

| Example No. | R¹ | R² | R³ | Melting point [°C.] |
|---|---|---|---|---|
| (III-10) | —CH₃ | H | pyrimidine with 4,6-di-OCH₃, 2-yl | 122 |
| (III-11) | —C₄H₉—sec. | H | pyrimidine with 4,6-di-OCH₃, 2-yl | 68 |
| (III-12) | —C₄H₉—i | H | pyrimidine with 4,6-di-OCH₃, 2-yl | 76 |
| (III-13) | —C₂H₅ | H | 4-methylpyrimidin-2-yl | 95 |
| (III-14) | —CH₂—COOC₂H₅ | H | 4-methylpyrimidin-2-yl | |
| (III-15) | —CH₂—(2-fluorophenyl) | H | 4-methylpyrimidin-2-yl | 205 |
| (III-16) | —CH₂—CH=CH₂ | H | 4-methylpyrimidin-2-yl | |
| (III-17) | —C₄H₉—n | H | 4-methylpyrimidin-2-yl | |
| (III-18) | —C₄H₉—sec. | H | 4-methylpyrimidin-2-yl | |

TABLE 2-continued $$\begin{array}{c} R^1O \\ | \\ HN \\ \diagdown \\ C-N \diagup R^2 \\ \diagup \quad \diagdown R^3 \\ HN \end{array} \quad (III)$$

| Example No. | R¹ | R² | R³ | Melting point [°C.] |
|---|---|---|---|---|
| (III-19) | —CH₂CH₂CH₂Cl | H | pyrimidin-2-yl with 4-CH₃ | 102 |
| (III-20) | —CH₃ | H | pyrimidin-2-yl with 4-OCH₃, 6-Cl | 112 |
| (III-21) | —CH₂—C₆H₅ | H | pyrimidin-2-yl with 4-OCH₃, 6-OCH₃ | 74 |
| (III-22) | —CH₃ | H | pyrimidin-2-yl | 107–109 |
| (III-23) | —CH₃ | H | pyrimidin-2-yl with 4-OC₂H₅, 6-OC₂H₅ | |
| (III-24) | —CH₂—C₆H₅ | H | pyrimidin-2-yl with 4-CH₃, 6-OCH₃ | n_D^{20}: 1,5645 |
| (III-25) | —CH₂—C₆H₅ | H | pyrimidin-2-yl with 6-C₂H₅ | 112 |
| (III-26) | —CH(C₆H₅)₂ | H | pyrimidin-2-yl with 4-CH₃ | 165 |
| (III-27) | —CH₂—C₆H₅ | H | pyrimidin-2-yl with 4-CH₃, 5-COOC₂H₅ | 130 |

TABLE 2-continued $$\underset{\text{HN}}{\overset{R^1O}{\underset{|}{HN}}}C-N\overset{R^2}{\underset{R^3}{}}$$ (III)

| Example No. | R¹ | R² | R³ | Melting point [°C.] |
|---|---|---|---|---|
| (III-28) | —CH₂CH₂OCH₃ | H | ![pyrimidinyl with CH₃] | 242 (decomposition) |
| (III-29) | —CH₂—CH=CH₂ | H | ![pyrimidinyl with CH₃, COOC₂H₅] | 143 |
| (III-30) | —CH₂—CH=CH₂ | H | ![pyrimidinyl with C₂H₅] | 83 |

Preparation of starting substances of the formula (IV)

EXAMPLE (IV-1)

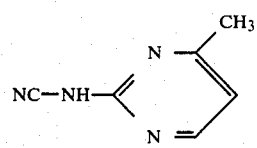

13.2 g (0.1 mole) of acetylacetaldehyde dimethyl acetal are added dropwise to a mixture of 8.4 g (0.1 mole) of dicyanodiamide, 5.4 g (0.1 mole) of sodium methylate and 100 ml of methanol at 20°–25° C., with stirring. The reaction mixture is heated under reflux for 2 hours. After the solvent has been distilled off, the crystalline residue is dissolved in 100 ml of water. The mixture is filtered. The filtrate is brought to pH = 3 with concentrated hydrochloric acid. The product precipitated as crystals is isolated by filtration with suction.

9.7 g (72% of theory) of 2-cyanoamino-4-methyl-pyrimidine of melting point 203° C. are obtained.

EXAMPLE (IV-2)

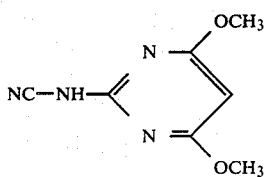

A solution, heated to 100° C., of 24 g (0.427mole) of potassium hydroxide in 100 ml of water is added to a mixture of 9.2 g (0.043 mole) of N-(4,6-dimethoxy-pyrimidin-2-yl)-thiourea and 70 ml of water at 100° C., with stirring. The mixture is subsequently stirred at 100° C. for 2 minutes and a solution, warmed to 100° C., of 16.2 g (0.05 mole) of lead(II) acetate in 30 ml of water is added. The mixture is heated under reflux for a further 5 minutes and then cooled to 0° C. to 5° C., and 30 ml of glacial acetic acid are added to the aqueous solution. The product thereby obtained as crystals is isolated by filtration with suction.

6.3 g (81.5% of theory) of 2-cyanoamino-4,6-dimethoxy-pyrimidine of melting point 202° C. are obtained.

The same result is obtained if the reaction is carried out in water/mathanol mixtures under otherwise identical conditions.

The compounds of the formula (IV) listed in the following Table 3 can be prepared by the processes described by way of example in the preceding examples:

TABLE 3

$$N\equiv C-N\overset{R^2}{\underset{R^3}{}}$$ (IV)

| Example No. | R² | R³ | Melting point [°C.] |
|---|---|---|---|
| (IV-3) | H | ![pyrimidinyl with OCH₃, CH₃] | 258 |
| (IV-4) | H | ![pyrimidinyl with OC₂H₅, CH₃] | — |

TABLE 3-continued $$\underset{R^3}{\overset{R^2}{N\equiv C-N}} \quad (IV)$$

| Example No. | R² | R³ | Melting point [°C.] |
|---|---|---|---|
| (IV-5) | H | (pyrimidine with SCH₃ and CH₃) | |
| (IV-6) | H | (pyrimidine with N(CH₃)₂ and CH₃) | |
| (IV-7) | H | (pyrimidine with OCHF₂ and CH₃) | 174 |
| (IV-8) | H | (pyrimidine with CH₃ and COCH₃) | 174 |
| (IV-9) | H | (pyrimidine with OH) | >300 |
| (IV-10) | H | (pyrimidine with C₂H₅) | 146 |
| (IV-11) | H | (pyrimidine with CH₃ and COOC₂H₅) | 126 |
| (IV-12) | H | (pyrimidine with OCH₃ and Cl) | 200 |
| (IV-13) | H | (pyrimidine with OC₂H₅ and OC₂H₅) | 235–237 |
| (IV-14) | H | (pyrimidine with Cl and OC₂H₅) | |
| (IV-15) | H | (pyrimidine with Cl and N(CH₃)₂) | |
| (IV-16) | H | (pyrimidine) | 186 |
| (IV-17) | H | (pyrimidine with OH and COOC₂H₅) | 220 (decomposition) |

2-(Alkyl-cyano-amino)-pyrimidines of the formula (IV) can be prepared, for example, as follows:

EXAMPLE (IV-18)

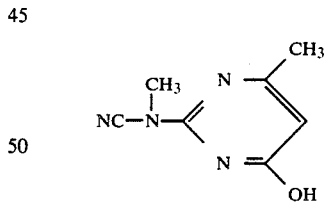

12.6 g (0.1 mole) of dimethyl sulphate are added dropwise to a solution of 15 g (0.1 mole) of 2-cyanoamino-4-hydroxy-6-methyl-pyrimidine—prepared by process (b) and 4.1 g (0.1 mole) of sodium hydroxide in 60 ml of water, whereupon the reaction temperature rises from 20° C. to 40° C. After the mixture has been stirred at 20° C. for 2 hours, the product obtained as crystals is isolated by filtration with suction.

11.1 g (68% of theory) of 2-(methyl-cyanoamino)-4-hydroxy-6-methyl-pyrimidine of melting point 290° C. are obtained.

The following compound is obtained analogously:

EXAMPLE (IV-19)

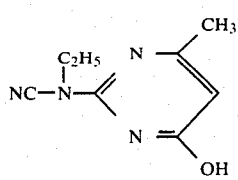

Melting point 215° C. to 220° C.

EXAMPLE (IV-20)

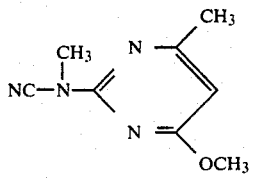

127.5 g (1 mole) of dimethyl sulphate are added dropwise to a solution of 75 g (0.5 mole) of 2-cyanoamino-4-hydroxy-6-methyl-pyrimidine—prepared by process (b)—and 44 g (1.1 mole) of sodium hydroxide in 750 ml of water, whereupon the reaction temperature rises from 20° C. to 35° C. After the mixture has been stirred at 20° C. for 12 hours, the pH is brought to a value of between 9 and 10 by addition of sodium hydroxide solution and the product obtained as crystals is isolated by filtration with suction.

13 g (15% of theory) of 2(methyl-cyanoamino)-4-methoxy-6-methyl-pyrimidine of melting point 123° C. are obtained.

The following compound is obtained analogously:

EXAMPLE (IV-21)

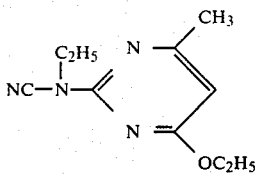

Melting point 71° C.

Preparation of the starting substances of the formula (X)

EXAMPLE (X-1)

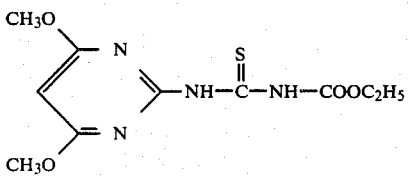

A mixture of 15.5 g (0.1 mole) of 2-amino-4,6-dimethoxy-pyrimidine, 13.1 g (0.1 mole) of ethoxycarbonylisothiocyanate and 200 ml of acetonitrile is stirred at 60° C. for 2 hours. It is then cooled to 10° C. and the product obtained as crystals is isolated by filtration with suction.

22.5 g (79% of theory) of 1-(ethoxycarbonyl)-3-(4,6-dimethoxy-pyrimidine-2-yl)-thiourea of melting point 194° C. (decomposition) are obtained.

The compounds of the formula (X) listed in the following Table 4 can be prepared by the process described by way of example in the preceding example:

TABLE 4

$$R^7-\underset{\underset{O}{\|}}{C}-NH-\underset{\underset{S}{\|}}{C}-NH-R^3 \quad (X)$$

| Example No. | $R^7$ | $R^3$ | Melting point [°C.] |
|---|---|---|---|
| (X-2) |  | 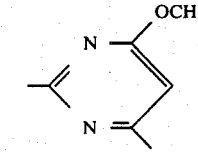 | 189 |
| (X-3) | 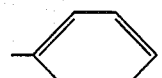 | 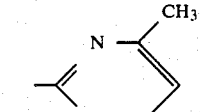 | 198–199 (decomposition) |
| (X-4) | —OC$_2$H$_5$ | 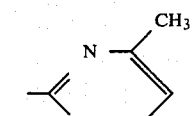 | 217 |
| (X-5) | 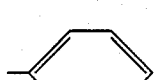 | 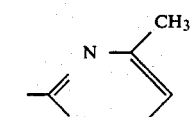 | 190 |
| (X-6) | —OC$_2$H$_5$ | 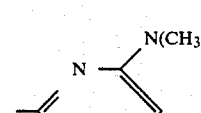 | 168 |
| (X-7) | 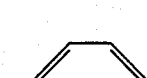 | 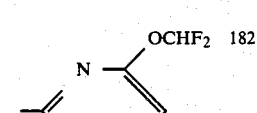 | 182 |
| (X-8) | —OC$_2$H$_5$ | 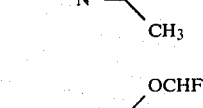 | 184–185 |

TABLE 4-continued $$\underset{R^7-\overset{O}{\overset{\|}{C}}-NH-\overset{S}{\overset{\|}{C}}-NH-R^3}{} \quad (X)$$

| Example No. | R⁷ | R³ | Melting point [°C.] |
|---|---|---|---|
| (X-9) | —OC₂H₅ | 4,6-bis(OCHF₂)-pyrimidin-2-yl | 173 |
| (X-10) | —OC₂H₅ | 4-OCH₃-6-Cl-pyrimidin-2-yl | 160–162 |
| (X-11) | —OC₂H₅ | 4-OC₂H₅-6-CH₃-pyrimidin-2-yl | |
| (X-12) | —OC₂H₅ | 4-SCH₃-6-CH₃-pyrimidin-2-yl | |
| (X-13) | —OC₂H₅ | 4-N(CH₃)₂-6-CH₃-pyrimidin-2-yl | |
| (X-14) | phenyl | pyrimidin-2-yl | 173 |
| (X-15) | phenyl | 4,6-bis(OC₂H₅)-pyrimidin-2-yl | 179 |
| (X-16) | —OC₂H₅ | 4,6-bis(OC₂H₅)-pyrimidin-2-yl | 159 |
| (X-17) | phenyl | 4-CH₃-6-OC₂H₅-pyrimidin-2-yl | 156 |
| (X-18) | phenyl | 4-CH₃-6-Cl-pyrimidin-2-yl | 144 |
| (X-19) | —OC₂H₅ | 4-CH₃-6-Cl-pyrimidin-2-yl | 122–124 |

Preparation of the starting substances of the formula (XI)

EXAMPLE (XI-1)

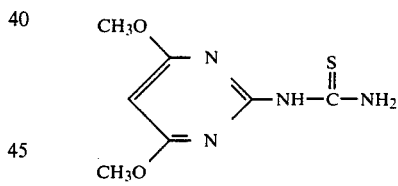

A mixture of 5.0 g (0.0175 mole) of 1-(ethoxycarbonyl)-3-(4,6-dimethoxy-pyrimidin-2-yl)-thiourea, 4.0 g (0.1 mole) of sodium hydroxide and 100 ml of water is stirred at 20° C. for 2 days. Dilute hydrochloric acid is then added dropwise, with stirring, until the solution has been rendered acid and the evolution of CO₂ has ended. The product obtained as crystals is isolated by filtration with suction.

3.5 g (94% of theory) of 4,6-dimethoxy-pyrimidin-2-yl-thiourea of melting point 245°–248° C. (decomposition) are obtained.

The compounds of the formula (XI) listed in the following Table 5 can be prepared by the process described by way of example in the preceding example:

TABLE 5

$$H_2N-\overset{\overset{S}{\|}}{C}-NH-R^3 \quad (XI)$$

| Example No. | $R^3$ | Melting point [°C.] |
|---|---|---|
| (XI-2) | 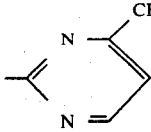 | 264–265 |
| (XI-3) | 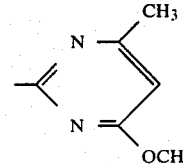 | 207 |
| (XI-4) | 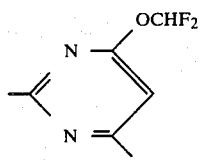 | 192–194 |
| (XI-5) | 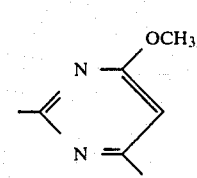 | 225–227 (decomposition) |
| (XI-6) | 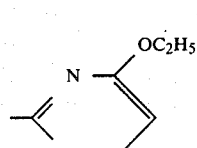 | |
| (XI-7) | 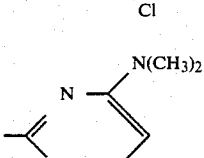 | |
| (XI-8) | 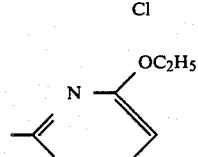 | |
| (XI-9) | 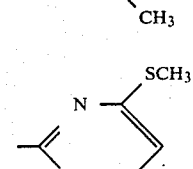 | |

TABLE 5-continued $$H_2N-\overset{\overset{S}{\|}}{C}-NH-R^3 \quad (XI)$$

| Example No. | $R^3$ | Melting point [°C.] |
|---|---|---|
| (XI-10) | 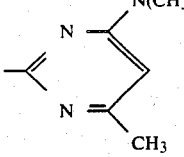 | |
| (XI-11) | 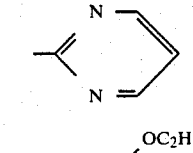 | 263 |
| (XI-12) | 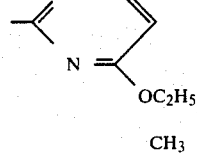 | 166 |
| (XI-13) | 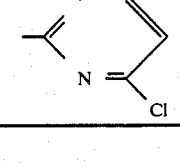 | >180 (decomposition) |

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control. The figures denote:
0%=no action (like untreated control)
100%=total destruction.

In this test, the active compounds according to the invention exhibit a very good herbicidal activity.

Example B

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5-15 cm are sprayed with the preparation of the active compound in such a way as to apply the particular amounts of active compound desired per unit area. The concentration of the spray liquor is so chosen that the particular amounts of active compound desired are applied in 2,000 of water/ha. After three weeks, the degree of damage to the plants is rated in damage in comparison to the development of the untreated control. The figures denote:
0%=no action (like untreated control)
100%=total destruction.

In this test, the active compounds according to the invention exhibit a very good herbicidal activity.

We claim:
1. A benzolactam-sultam of the formula

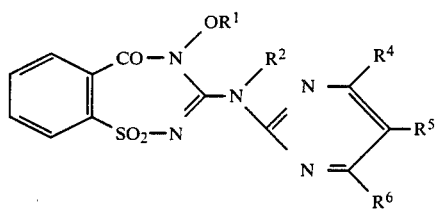

in which
R$^1$ represents C$_1$-C$_{12}$-alkyl (which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkyl-carbonyl, C$_1$-C$_4$-alkoxy-carbonyl, C$_1$-C$_4$-alkylamino-carbonyl or di-(C$_1$-C$_4$-alkyl)-amino-carbonyl, or represents C$_3$-C$_6$-alkenyl (which is optionally substituted by fluorine, chlorine, or bromine), C$_3$-C$_6$-alkinyl, C$_3$-C$_6$-cycloalkyl, C$_3$-C$_6$-cycloalkyl-C$_1$-C$_2$-alkyl or phenyl-C$_1$-C$_2$-alkyl (which is optionally substituted by fluorine, chlorine, nitro, cyano, C$_1$-C$_4$alkyl, C$_1$-C$_4$-alkoxy or C$_1$-C$_4$-alkoxy-carbonyl) or represents phenyl (which is optionally substituted by fluorine, chlorine, nitro, cyano, C$_1$-C$_4$-alkyl, trifluoromethyl, C$_1$-C$_4$-alkoxy, C$_1$-C$_2$-fluoroalkoxy, C$_1$-C$_4$-alkylthio, trifluoromethylthio or C$_1$-C$_4$-alkoxy-carbonyl), R$^2$ represents hydrogen or C$_1$-C$_4$-alkyl (which is optionally substituted by fluorine, chlorine, cyano, C$_1$-C$_4$-alkoxy, C$_1$-C$_4$-alkylthio, C$_1$-C$_4$-alkylsulphinyl, C$_1$-C$_4$-alkylsulphonyl, C$_1$-C$_4$-alkylcarbonyl, C$_1$-C$_4$-alkoxy-carbonyl, C$_1$-C$_4$-alkylamino-carbonyl or di-(C$_1$-C$_4$-alkyl)-amino-carbonyl), or represents C$_3$-C$_6$-alkenyl, C$_3$-C$_6$-alkinyl or phenyl C$_1$-C$_2$-alkyl (which is optionally substituted by fluorine, chlorine, nitro, cyano, C$_1$-C$_4$-alkyl, C$_1$-C$_4$ alkoxy or C$_1$-C$_4$-alkoxy-carbonyl), R$^4$ represents hydrogen, hydroxyl, fluorine, chlorine or bromine or represents C$_1$-C$_4$-alkyl, C$_1$-C$_4$alkoxy or C$_1$-C$_4$-alkylthio (which are optionally substituted by fluorine and/or chlorine), R$^5$ represents hydrogen, fluorine, chlorine, bromine, cyano, formyl or C$_1$-C$_4$-alkyl (which is optionally substituted by fluorine and/or chlorine) or represents C$_1$-C$_4$-alkyl-carbonyl or C$_1$-C$_4$-alkoxycarbonyl and R$^6$ represents hydrogen, amino or C$_1$-C$_4$-alkyl (which is optionally substituted by fluorine and/or chlorine) or represents C$_1$-C$_4$-alkoxy (which is optionally substituted by fluorine and/or chlorine or represents C$_1$-C$_4$-alkyl-amino or di-(C$_1$-C$_4$-alkyl)-amino, with the proviso that R$^4$ and R$^5$ do not simultaneously represent methyl.

2. A benzolactam-sultam according to claim 1, in which
R1 represents C$_1$-C$_8$-alkyl (which is optionally substituted by fluorine or chlorine), C$_3$-C$_4$-alkenyl, C$_1$-C$_2$-alkoxy-carbonylmethyl, phenethyl or benzyl (which is optionally substituted by fluorine, chlorine, nitro, cyano, methyl, methoxy or methoxycarbonyl), R$^2$ represents hydrogen, R$^4$ represents hydrogen, chlorine or C$_1$-C$_2$-alkoxy (which is optionally substituted by fluorine and/or chlorine), R$^5$ represents hydrogen, methylcarbonyl or C$_1$-C$_2$-alkoxy-carbonyl and R$^6$ represents hydrogen, C$_1$-C$_2$-alkyl (which is optionally substituted by fluorine and/or chlorine or C$_1$-C$_2$-alkoxy (which is optionally substituted by fluorine and/or chlorine).

3. A compound according to claim 1, wherein such compound is

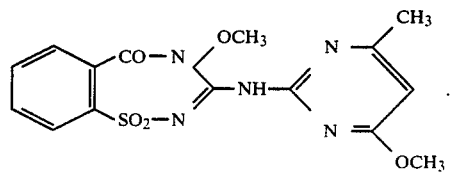

4. A compound according to claim 1, wherein such compound is

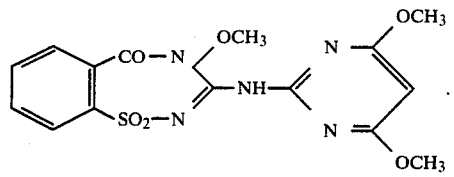

5. A compound according to claim 1, wherein such compound is

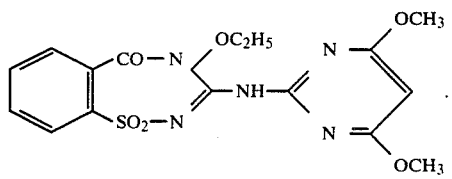

6. A compound according to claim 1, wherein such compound is

7. A compound according to claim 1, wherein such compound is

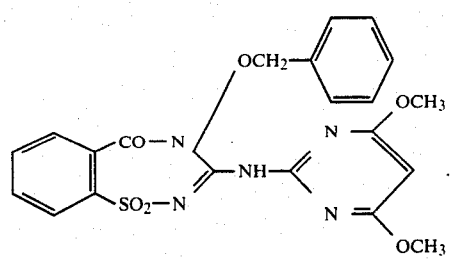

8. A herbicidal composition comprising a herbicidally effective amount of a compound according to claim 1 in admixture with a diluent.

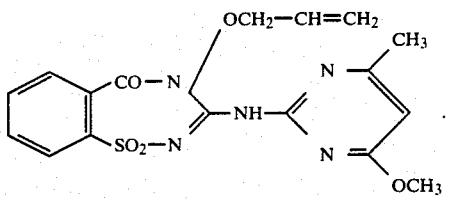

9. A method of combating unwanted vegetation which comprises applying to such vegetation or to a locus from which it is desired to exclude such vegetation a herbicidally effective amount of a compound according to claim 1.

10. A process for the preparation of a benzolactam-sultam according to claim 1, which comprises reacting 2-chlorosulphonyl-benzoyl chloride of the formula

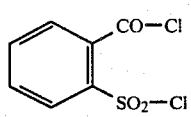

with an oxyguanidine derivative of the formula

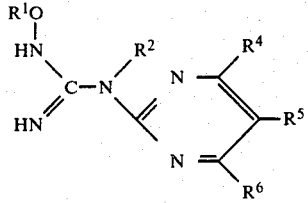

in the presence of an acid acceptor.

* * * * *